United States Patent [19]
Kucherlapati et al.

[11] Patent Number: 5,939,598
[45] Date of Patent: Aug. 17, 1999

[54] METHOD OF MAKING TRANSGENIC MICE LACKING ENDOGENOUS HEAVY CHAINS

[75] Inventors: Raju Kucherlapati, Darien, Conn.; Aya Jakobovits, Menlo Park, Calif.

[73] Assignee: Abgenix, Inc., Fremont, Calif.

[21] Appl. No.: 07/922,649

[22] Filed: Jul. 30, 1992

Related U.S. Application Data

[63] Continuation of application No. 07/610,515, Nov. 8, 1990, abandoned, which is a continuation-in-part of application No. 07/466,008, Jan. 12, 1990, abandoned.

[51] Int. Cl.$^6$ .......................... A61K 48/00; C12N 15/09
[52] U.S. Cl. ................... 800/25; 800/3; 800/21; 800/8
[58] Field of Search .................. 800/2, 21, 25; 435/172.3; 536/23.53

[56] References Cited

U.S. PATENT DOCUMENTS

| | | | |
|---|---|---|---|
| 4,950,599 | 8/1990 | Bertling | 435/456 |
| 4,959,313 | 9/1990 | Taketo | 435/69.1 |
| 5,204,244 | 4/1993 | Fell | 435/69.3 |
| 5,545,806 | 8/1996 | Lariberg | 800/2 |
| 5,591,669 | 1/1997 | Krimpenfnt | 800/2 |

FOREIGN PATENT DOCUMENTS

| | | |
|---|---|---|
| 0 298 807 A1 | 6/1988 | European Pat. Off. . |
| 322240 | 6/1989 | European Pat. Off. . |
| 0 459 372 A3 | 5/1991 | European Pat. Off. . |
| WO 90/04036 | 4/1990 | WIPO . |
| WO 92/03918 | 3/1992 | WIPO . |
| WO 94/02602 | 2/1994 | WIPO . |

OTHER PUBLICATIONS

Thomas et al Cell 51: 503, 1987. Cox Declaration from (998, 860) now USPN 5,545,806 Dec. 8, 1997.
Bruggemann et al PNAS 86: 6709, 1989 Nature Genetics 3: 88, 1994 Dec. 8, 1997.
Nature Genetics 7: 13, 1994.
Nature Genetics 7: 162, 1994, Dec. 8, 1997.
Thomas et al Cell 51: 503, 1987.
Berman et al EMBO J 7(3): 727, 1988.
Capecchi et al., "Altering The Genome By Homologous Recombination," Science, 244, pp. 1288–1292 (1989).
Choi et al., "RNA Splicing Generates A Variant Light Chain From An Aberrantly Arranged κ Gene," Nature, 286, pp. 776–779 (1980).
Doetschman et al., "Targeted Mutation Of The Hprt Gene in Mouse Embryonic Stem Cells," Proc. Natl. Acad. Sci., 85, pp. 8583–8587 (1988).
Johnson et al., "Targeting Of Nonexpressed Genes in Embryonic Stem Cells Via Homologous Recombination," Science, 245, pp. 1234–1236 (1989).
Kucherlapati et al., "Homologous recombination in mammalian somatic cells," Prog. Nucleic Acid Res. Mol. Biol., 36, pp. 301–310 (1989).
Mansour et al., "Disruption of the Proto–oncogene Int–2 In Mouse Embryo–derviced Stem Cells: A General Stratgegy For Targeting Mutations To Non–selectable Genes," Nature, 336, pp. 348–352 (1988).
Max et al., "Sequences of Five Potential Recombination Sites Encoded Close To An Immunoglobulin κ Constant Region Gene," Proc. Natl. Acad. Sci., 76, pp. 3450–3454 (1979).
Orkin et al., "Mutation In An Intervening Sequence Splice Junction In Man," Proc. Natl. Acad. Sci., 78, pp. 5041–5045 (1981).
Rajewski et al., "Evolutionary and Somatic Selection of the Antibody Repertoire in the Mouse," Science, 238, pp. 1088–1094 (1987).
Ramirez–Solis et al., "Chromosome Engineering In Mice," Nature, 378, pp. 720–724 (1995).
Sakano et al., "Sequences At The Somatic Recombination Sites Of Immunoglobulin Light–Chain Genes," Nature, 280, pp. 288–294 (1979).
Sakano et al., "Two Types Of Somatic Recombination Are Necessary For The Generation Of Complete Immunoglobulin Heavy–Chain Genes," Nature, 280, pp. 676–683 (1980).
Schwartzberg et al., "Germ–line Transmission Of A c–abl Mutation Produced By Targeted Gene Disruption In ES Cells," Science, 246, pp. 799–803 (1989).
Seidman and Leder, "A Mutant Immunoglobulin Light Chain Is Formed By Aberrant DNA–and RNA–Splicing Events," Nature, 286, pp. 779–783 (1980).

Treisman et al., "Specific Transcription and RNA Splicing Defects In Five Cloned β–Thalassaemia Genes," Nature, 302, pp. 591–596 (1983).

Zjilstra et al., "Germ–line Transmission Of A Disrupted β2–Microglobulin Gene Produced By Homologuous Recombination In Embryonic Stem Cells," Nature, 342, pp. 435–438 (1989).

Thomas et al.; Cell, vol. 51:503–512 (1987); Site–Directed Mutagenesis by Gene Targeting in Mouse Embryo–Derived Stem Cells.

Koller et al.; Proc. Natl. Acad. Sci. USA, vol. 86:8932–8935 (1989); Inactivating the $β_2$–microglobulin locus in mouse embryonic stem cells by homologous recombination.

Berman et al.; EMBO Journal, 7(3):727–738 (1988); Content and Organization of the human Ig $V_H$ locus: definition of three new $V_H$ families and linkage to the Ig $C_H$ locus.

Burke et al.; Science, 236:806–812 (1987); Cloning of Large Segments of Exogenous DNA into Yeast by Means of Artifical Chromosome Vectors.

Garza et al.; Science 246:641–646 (1989); Mapping the Drosophila Genome with Yeast Artificial Chromosomes.

Brownstein et al.; Science 244:1348–1351 (1989); Isolation of Single–Copy Human Genes from a Library of Yeast Artificial Chromosome Clones.

Sakano et al.; Nature 290:562–565 (1981); Identification and Nucleotide Sequence of a Diversity DNA Segment (D) of Immunoglobulin Heavy–Chain Genes.

Tucker et al.; Proc. Natl. Acad. Sci. USA 78(12):7684–7688 (1981); Mouse IgA Heavy Chain Gene Sequence: Implications for Evolution of Immunoglobulin Hinge Exons.

Blankenstein and Kruwinkel; Eur. J. Immunol. 17:1351–1357 (1987).

Joyner et al.; Nature 338:153–155 (1989).

Traver et al.; Proc. Nat. Acad. Sci. USA 86:5898–5902 (1989).

Panchis et al. Proc. Nat. Acad. Sci. USA 87:5109–5113 (1990).

Bruggemann et al., Proc. Natl. Acad. Sci. USA 86:6709–6713 (1989); A Repertoire of Monoclonal antibodies with Human Heavy Chains from Transgenic Mice.

Buttin G.; Trends in Genetics 3(8):205–206 (1987); Exogenous Ig Gene Rearrangement in Transgenic Mice: A New Strategy for Human Monocloanl Antibody Production.

Yancopoulos et al.; Science 241 1581–1583 (1988); Reconstruction of an Immune System.

Dorfman, Nickolas A., 1985, "The Optimal Technological Approach to the Development of Human Hybridomas," *Journal of Biological Response Modifiers,* 4:213–239.

Taggart et al., 1983, "Stable Antibody–Producing Murine Hybridomas," *Science* 219:1228–1230.

Yamamura, et al., PNAS USA (1986) 83, 2152–2156.

Koller, et al., PNAS USA (1989) 86, 8932–8935.

Shimizu, et al., PNAS USA (1989) 86, 8020–8023.

*Primary Examiner*—Deborah Crouch
*Assistant Examiner*—Karen M. Hauda
*Attorney, Agent, or Firm*—Fish & Neave; James F. Haley, Jr. Esq.; Jane T. Gunnison, Esq.

[57] ABSTRACT

The subject invention provides non-human mammalian hosts characterized by inactivated endogenous Ig loci. The hosts are produced by repetitive transformations of embryonic stem cells by homologous recombination, preferably in conjunction with breeding. Different strategies are employed for recombination of the human loci randomly or at analogous host loci.

13 Claims, 7 Drawing Sheets

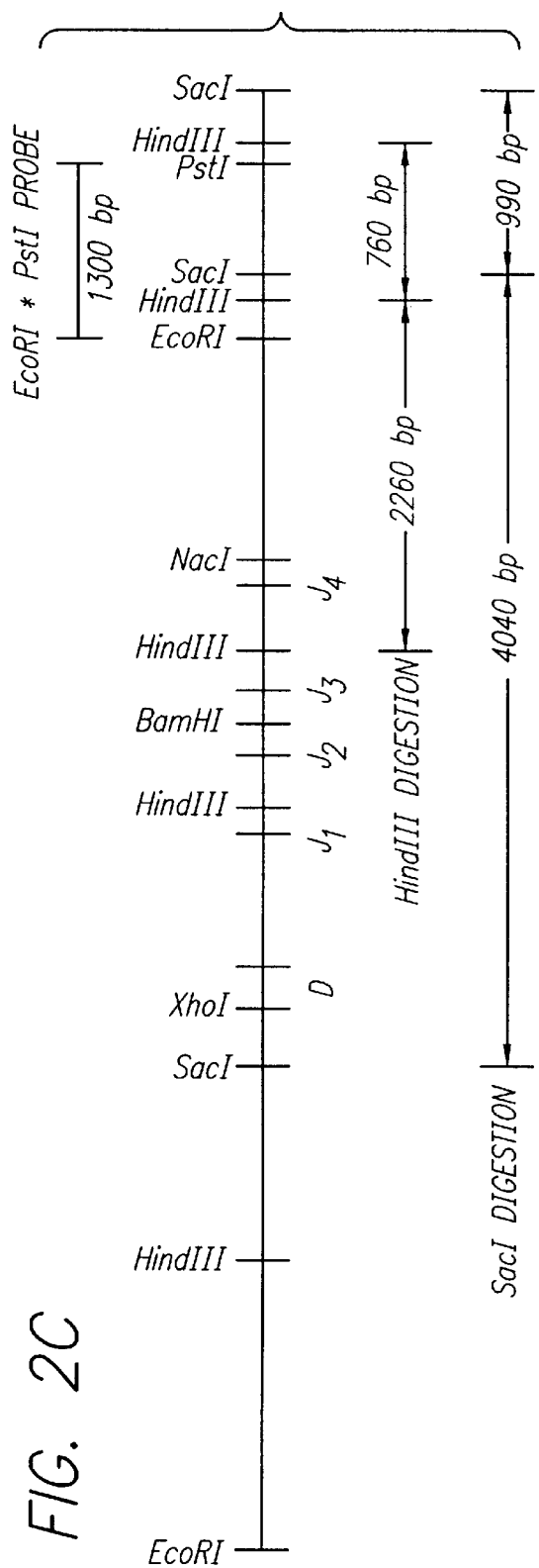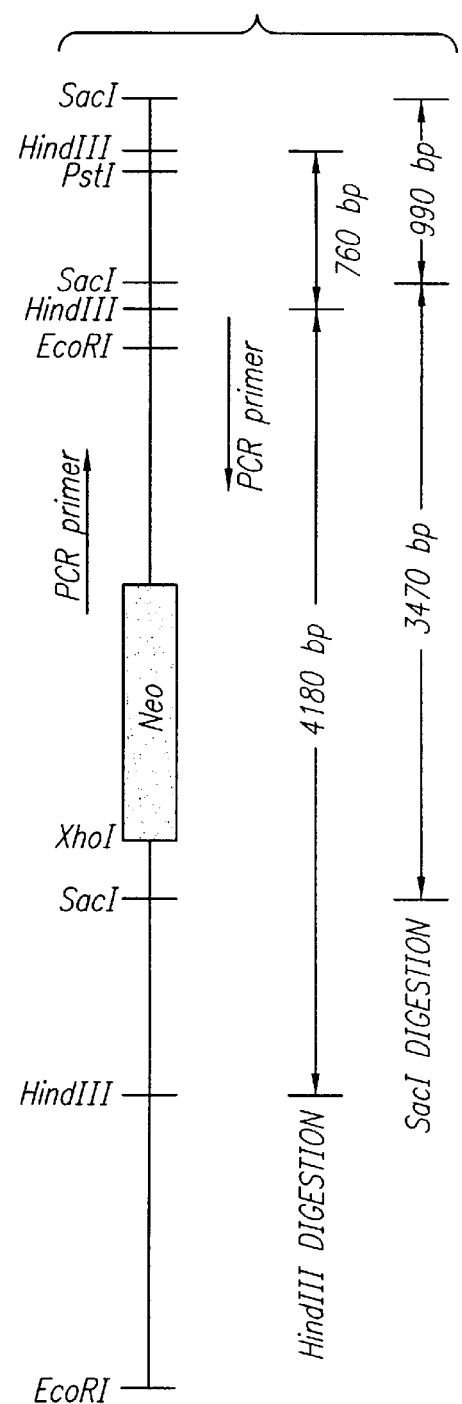

METHOD OF MAKING TRANSGENIC MICE LACKING ENDOGENOUS HEAVY CHAINS

CROSS-REFERENCE TO RELATED APPLICATIONS

This is a continuation of application Ser. No. 07/610,515 filed Nov. 8, 1990, now abandoned, which is a continuation-in-part of application Ser. No. 07/466,008 filed Jan. 12, 1990, now abandoned.

INTRODUCTION

1. Technical Field

The field of this invention is the production of xenogeneic specific binding proteins in a viable mammalian host.

2. Background

Monoclonal antibodies find use in both diagnosis and therapy. Because of their ability to bind to a specific epitope, they can be uniquely used to identify molecules carrying that epitope or may be directed, by themselves or in conjunction with another moiety, to a specific site for diagnosis or therapy.

Monoclonal antibodies comprise heavy and light chains which join together to define a binding region for the epitope. Each of the chains is comprised of a variable region and a constant region. The constant region amino acid sequence is specific for a particular isotype of the antibody, as well as the host which produces the antibody.

Because of the relationship between the sequence of the constant region and the species from which the antibody is produced, the introduction of a xenogeneic antibody into the vascular system of the host can produce an immune response. Where the xenogeneic antibody may be introduced repetitively, in the case of chronic diseases, it becomes impractical to administer the antibody, since it will be rapidly destroyed and may have an adverse effect. There have been, therefore, many efforts to provide a source of syngeneic or allogeneic antibodies. One technique has involved the use of recombinant DNA technology where the genes for the heavy and light chains from the host were identified and the regions encoding the constant region isolated. These regions were then joined to the variable region encoding portion of other immunoglobulin genes from another species directed to a specific epitope.

While the resulting chimeric partly xenogeneic antibody is substantially more useful than using a fully xenogeneic antibody, it still has a number of disadvantages. The identification, isolation and joining of the variable and constant regions requires substantial work. In addition, the joining of a constant region from one species to a variable region from another species may change the specificity and affinity of the variable regions, so as to lose the desired properties of the variable region. Also, there are framework and hypervariable sequences specific for a species in the variable region. These framework and hypervariable sequences may result in undesirable antigenic responses.

It would therefore be more desirable to produce allogeneic antibodies for administration to a host by immunizing the host with an immunogen of interest. For primates, particularly humans, this approach is not practical. The human antibodies which have been produced have been based on the adventitious presence of an available spleen, from a host which had been previously immunized to the epitope of interest. While human peripheral blood lymphocytes may be employed for the production of monoclonal antibodies, these have not been particularly successful in fusions and have usually led only to IgM. Moreover, it is particularly difficult to generate a human antibody response against a human protein, a desired target in many therapeutic and diagnostic applications. There is, therefore, substantial interest in finding alternative routes to the production of allogeneic antibodies for humans.

Relevant Literature

Thomas and Capecchi, *Cell*, 51, 503–512, 1987. Koller and Smithies, *Proc. Natl. Acad. Sci. USA*, 86, 8932–8935, 1989, describe inactivating the B2microglobulin locus by homologous recombination in embryonic stem cells. Berman et al., *EMBO J.* 7, 727–738, 1988, describe the human Ig VH locus. Burke, et al., *Science*, 236, 806–812, 1987, describe yeast artificial chromosome vectors. See also, Garza et al., *Science*, 246, 641–646, 1989, and Brownstein et al., *Science*, 244, 1348–1351, 1989. Sakano, et al., describe a diversity segment of the immunoglobulin heavy chain genes. Sakano et al., *Nature*, 290, 562–565, 1981. Tucker et al., *Proc. Natl. Acad. Sci. USA*, 78, 7684–7688, 1981, describe the mouse IgA heavy chain gene sequence. Blankenstein and Kruwinkel *Eur. J. Immunol.*, 17, 1351–1357, 1987, describe the mouse variable heavy chain region. See also, Joyner et al., *Nature*, 338, 153–155, 1989, Traver et al., *Proc. Nat. Acad. Sci. USA* 86, 5898–5902, 1989, and Panchis et al., *Proc. Nat. Acad. Sci. USA*, 87, 5109–5113, 1990.

SUMMARY OF THE INVENTION

Xenogenic specific binding proteins are produced in a non-primate viable mammalian host by immunization of the mammalian host with an appropriate immunogen.

The host is characterized by: (1) being incapable of producing endogenous immunoglobulin; (2) an exogenous immunoglobulin locus comprising at least one immunoglobulin constant region, or protein thereof, immunoglobulin sequences providing for the components of the variable region of at least one of the light and heavy chains, and at least one intron with appropriate splicing sites for excision and assembly of a functional immunoglobulin subunit. Thus, the mammalian host will comprise at least one xenogeneic constant region or protein thereof capable of being spliced to a functional J region of an endogenous or exogenous immunoglobulin locus, may have an entire immunoglobulin locus of the host substituted by a portion or an entire xenogeneic immunoglobulin locus, or may have a xenogeneic immunoglobulin locus inserted into a chromosome of the host cell and an inactivated endogenous immunoglobulin region. These various alternatives will be achieved, at least in part, by employing homologous recombination at the immunoglobulin loci for the heavy and light chains.

BRIEF DESCRIPTION OF THE DRAWINGS

FIG. 1A depicts an EcoRl fragment of a mouse immunoglobulin heavy chain locus containing the mouse heavy chain J genes.

FIGS. 2A–2D:

FIG. 2A depicts an EcoRl fragment of a mouse immunoglobulin heavy chain locus containing the mouse heavy chain J genes. FIG. 2B depicts inactivation vector pmHδJ. FIG. 2C depicts the results of Southern analysis of wild type mouse immunoglobulin heavy chain locus by HindIII and SacI digestion. FIG. 2D depicts the results of Southern analysis of a targeted mouse immunoglobulin heavy chain locus by HindIII and SacI digestion.

FIG. 3A is a schematic representation of a human immunoglobulin heavy chain locus and restriction fragments thereof. FIG. 3B is a schematic representation of a mouse immunoglobulin heavy chain locus showing the J558 and Cε-Cα fragments. FIG. 3C depicts a human heavy chain replacement YAC vector.

DESCRIPTION OF SPECIFIC EMBODIMENTS

Figure 1A:
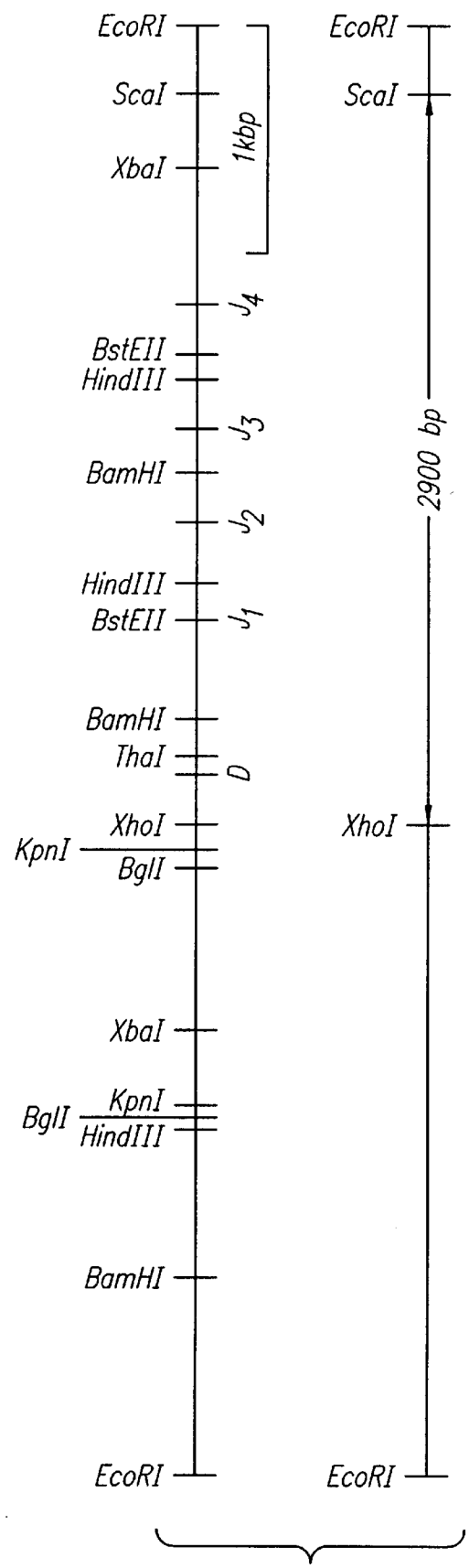
FIGS. 1A&B.

Novel transgenic mammalian hosts, other than primates, particularly other than human, are provided, where the host is capable of mounting an immune response to an immunogen, where the response produces antibodies having primate, particularly human, constant and/or variable regions or such other effector peptide sequences of interest. The hosts are characterized by being capable of producing xenogeneic or modified antibodies as a result of substitution and/or inactivation of the endogenous immunoglobulin subunit encoding loci. The modifications retain at least a portion of the constant regions which provide for assembly of the variable region binding site bonded at the C-terminus to a functional peptide. The functional peptide may take many forms or conformations and may serve as an enzyme, growth factor, binding protein, ligand, cytokine, effector protein, chelating proteins, etc. The antibodies may be any isotype, e.g., IgA, D, E, G or M or subtypes within the isotype.

A number of strategies may be employed to achieve the desired transgenic hosts. Various transgenic hosts may be employed, particularly murine, lagomorpha, ovine, porcine, equine, canine, feline, or the like, normally other than primate. For the most part, mice have been used for the production of B-lymphocytes for immortalization for the production of antibodies. Since mice are easy to handle, can be produced in large quantities, and are known to have an extensive immune repertoire, mice will usually be the animal of choice. Therefore, in the following discussion, the discussion will refer to mice, but it should be understood that other animals, particularly mammals, may be readily substituted for the mice, following the same procedures.

In one strategy, as individual steps, the human heavy and light chain immunoglobulin gene complexes are introduced into the mouse germ line and in a separate step the corresponding mouse genes are rendered non-functional. Human heavy and light chain genes are reconstructed in an appropriate eukaryotic or prokaryotic microorganism and the resulting DNA fragments can be introduced into pronuclei of fertilized mouse oocytes or embryonic stem cells. Inactivation of the endogenous mouse immunoglobulin loci is achieved by targeted disruption of the appropriate loci by homologous recombination in mouse embryonic stem cells. In each case chimeric animals are generated which are derived in part from the modified embryonic stem cells and are capable of transmitting the genetic modifications through the germ line. The mating of mouse strains with human immunoglobulin loci to strains with inactivated mouse loci will yield animals whose antibody production is purely human.

In the next strategy, fragments of the human heavy and light chain immunoglobulin loci are used to directly replace the corresponding mouse loci by homologous recombination in mouse embryonic stem cells. This is followed by the generation of chimeric transgenic animals in which the embryonic stem cell-derived cells contribute to the germ line.

These strategies are based on the known organization of the immunoglobulin chain loci in a number of animals, since the organization, relative location of exons encoding individual domains, and location of splice sites and transcriptional elements, is understood to varying degrees. In the human, the immunoglobulin heavy chain locus is located on chromosome 14. In the 5'–3' direction of transcription, the locus comprises a large cluster of variable region genes ($V_H$), the diversity (D) region genes, followed by the joining ($J_H$) region genes and the constant ($C_H$) gene cluster. The size of the locus is estimated to be about 2,500 kilobases (kb). During B-cell development, discontinuous gene segments from the germ line IgH locus are juxtaposed by means of a physical rearrangement of the DNA. In order for a functional heavy chain Ig polypeptide to be produced, three discontinuous DNA segments, from the $V_H$, D, and $J_H$ regions must be joined in a specific sequential fashion; $V_H$ to $DJ_H$, generating the functional unit $V_H DJ_H$. Once a $V_H DJ_H$ has been formed, specific heavy chains are produced following transcription of the Ig locus, utilizing as a template the specific $V_H DJ_H C_H$ unit comprising exons and introns. There are two loci for Ig light chains, the κ locus on human chromosome 2 and the λ locus on human chromosome 22. The structure of the IgL loci is similar to that of the IgH locus, except that the D region is not present. Following IgH rearrangement, rearrangement of a light chain locus is similarly accomplished by $V_L$ and $J_L$ joining of the κ or λ chain. The sizes of the λ and κ loci are each approximately 1000 kb. Expression of rearranged IgH and an Igκ or Igλ light chain in a particular B-cell allows for the generation of antibody molecules.

In order to isolate, clone and transfer the $IgH_{hu}$ locus, a yeast artificial chromosome may be employed. The entire $IgH_{hu}$ locus can be contained within one or a few yeast artificial chromosome (YAC) clones. The same is true for the Ig light chain loci. Subsequent introduction of the appropriate heavy chain or light chain YAC clones into recipient yeast allows for the reconstitution of intact germ line Ig loci by homologous recombination between overlapping regions of homology. In this manner, the isolation of DNA fragments encoding the human Ig chain is obtained.

Figure 1B:
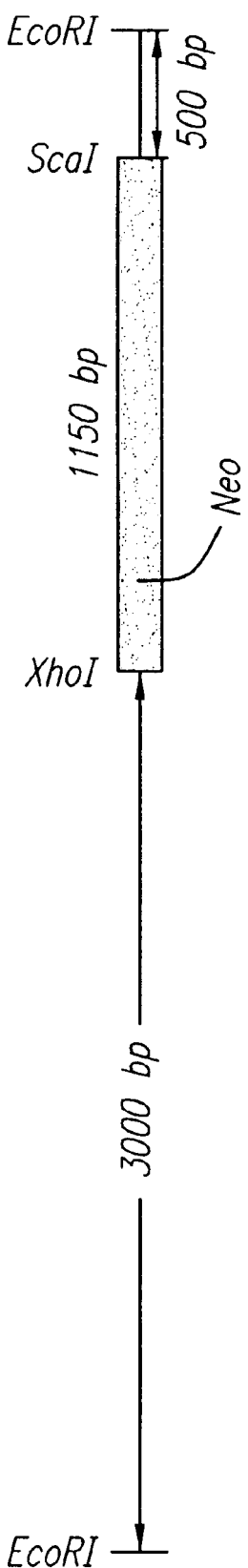
FIG. 1B depicts a portion of inactivation vector mDδJ.Neo.

In order to obtain a broad spectrum of high affinity antibodies, it is not necessary that one include the entire V region. Various V region gene families are interspersed within the V region cluster. Thus, by obtaining a subset of the known V region genes of the human heavy and light chain Ig loci (Berman et al., EMBO J. (1988) 7: 727–738) rather than the entire complement of V regions, the transgenic host may be immunized and be capable of mounting a strong immune response and provide high affinity antibodies. In this manner, relatively small DNA fragments of the chromosome may be employed, for example, a reported 670 kb fragment of the $Ig_{Hu}$ locus is shown in FIG. 1b. This NotI-NotI restriction fragment would serve to provide a variety of V regions, which will provide increased diversity by recombining with the various D and J regions and undergoing somatic mutation.

In order to provide for the production of human antibodies in a xenogeneic host, it is necessary that the host be competent to provide the necessary enzymes and other factors involved with the production of antibodies, while lacking competent endogenous genes for the expression of heavy and light subunits of immunoglobulins. Thus, those enzymes and other factors associated with germ line rearrangement, splicing, somatic mutation, and the like, will be functional in the xenogeneic host. What will be lacking is a functional natural region comprising the various exons associated with the production of endogenous immunoglobulin subunits.

The human DNA may be introduced into the pronuclei of fertilized oocytes or embryonic stem cells. The integration may be random or homologous depending on the particular strategy to be employed. Thus, by using transformation, using repetitive steps or in combination with breeding, transgenic animals may be obtained which are able to produce human antibodies in the substantial absence of light or heavy host immunoglobulin subunits.

To inactivate the host immunoglobulin loci, homologous recombination may be employed, where DNA is introduced at the immunoglobulin heavy chain and light chain loci which inhibits the production of endogenous immunoglobulin subunits. Since there are two heavy chain alleles and two light chain loci, each with two alleles, although one may choose to ignore the λ loci, there will have to be multiple transformations which result in inactivation of each of the alleles. (By transformation is intended any technique for introducing DNA into a viable cell, such as conjugation, transformation, transfection, transduction, electroporation, lipofection, Biolistics, or the like.) Homologous recombination may be employed to functionally inactivate each of the loci, by introduction of the homologous DNA into embryonic stem cells, followed by introduction of the modified cells into recipient blastocysts. Subsequent breeding allows for germ line transmission of the inactivated locus. One can therefore choose to breed heterozygous offspring and select for homozygous offspring from the heterozygous parents or again one may use the embryonic stem cell for homologous recombination and inactivation of the comparable locus.

The number of transformation steps may be reduced by providing at least a fragment of the human immunoglobulin subunit locus for homologous recombination with the analogous endogenous immunoglobulin, so that the human locus is substituted for at least a part of the host immunoglobulin locus, with resulting inactivation of the host immunoglobulin subunit locus. Of particular interest is the use of transformation for a single inactivation, followed by breeding of the heterozygous offspring to produce a homozygous offspring. Where the human locus is employed for substitution or insertion into the host locus for inactivation, the number of transformations may be limited to three transformations and as already indicated, one may choose to ignore the less used λ locus and limit the transformations to two transformations. Alternatively, one may choose to provide for inactivation as a separate step for each locus, employing embryonic stem cells from offspring which have previously had one or more loci inactivated. In the event only transformation is used and the human locus is integrated into the host genome in random fashion, a total of eight transformations may be required.

For inactivation, any lesion in the target locus resulting in the prevention of expression of an immunoglobulin subunit of that locus may be employed. Thus, the lesion may be in a region comprising the enhancer, e.g., 5' upstream or intron, in the V, J or C regions, and with the heavy chain, the opportunity exists in the D region, or combinations thereof. Thus, the important factor is that Ig germ line gene rearrangement is inhibited, or a functional message encoding the immunoglobulin subunit cannot be produced, either due to failure of transcription, failure of processing of the message, or the like.

Preferably, when one is only interested in inactivating the immunoglobulin subunit locus, the lesion will be introduced into the J region of the immunoglobulin subunit locus. Thus, one produces a construct which lacks a functional J region and may comprise the sequences of the J region adjacent to and upstream and/or downstream from the J region or comprises all or part of the region with an inactivating insertion in the J region. The insertion may be 50 bp or more, where such insertion results in disruption of formation of a functional mRNA. Desirably, the J region in whole or substantial part, usually at least about 75% of the locus, preferably at least about 90% of the locus, is deleted. If desired, the lesion between the two flanking sequences defining the homologous region may extend beyond the J region, into the variable region and/or into the constant region.

Desirably, a marker gene is used to replace the J region. Various markers may be employed, particularly those which allow for positive selection. Of particular interest is the use of G418 resistance, resulting from expression of the gene for neomycin phosphotransferase.

Upstream and/or downstream from the target gene construct may be a gene which provides for identification of whether a double crossover has occurred. For this purpose, the Herpes simplex virus thymidine kinase gene may be employed, since cells expressing the thymidine kinase gene may be killed by the use of nucleoside analogs such as acyclovir or gancyclovir, by their cytotoxic effects on cells that contain a functional HSV-tk gene. The absence of sensitivity to these nucleoside analogs indicates the absence of the HSV-thymidine kinase gene and, therefore, where homologous recombination has occurred, that a double crossover has also occurred.

While the presence of the marker gene in the genome will indicate that integration has occurred, it will still be necessary to determine whether homologous integration has occurred. This can be achieved in a number of ways. For the most part, DNA analysis will be employed to establish the location of the integration. By employing probes for the insert and then sequencing the 5' and 3' regions flanking the insert for the presence of the target locus extending beyond the flanking region of the construct or identifying the presence of a deletion, when such deletion has been introduced, the desired integration may be established.

The polymerase chain reaction (PCR) may be used with advantage in detecting the presence of homologous recombination. Probes may be used which are complementary to a sequence within the construct and complementary to a sequence outside the construct and at the target locus. In this way, one can only obtain DNA chains having both the primers present in the complementary chains if homologous recombination has occurred. By demonstrating the presence of the probes for the expected size sequence, the occurrence of homologous recombination is supported.

The construct may further include a replication system which is functional in the mammalian host cell. For the most part, these replication systems will involve viral replication systems, such as Simian virus 40, Epstein-Barr virus, polyoma virus, papilloma virus, and the like. Various transcriptional initiation systems may be employed, either from viruses or from mammalian genes, such as SV40, metallathionein-I and II genes, β-actin gene, adenovirus early and late genes, phosphoglycerate kinase gene, RNA polymerase II gene, or the like. In addition to promoters, wild-type enhancers may be employed to further enhance the expression of the marker gene.

In constructing the subject constructs for homologous recombination, a replication system for procaryotes, particularly E. coli, may be included, for preparing the construct, cloning after each manipulation, analysis, such as restriction mapping or sequencing, expansion and isolation of the desired sequence. Where the construct is large, generally exceeding about 50 kbp, usually exceeding 100 kbp, and usually not more than about 1000 kbp, a yeast artificial chromosome (YAC) may be used for cloning of the construct.

Once a construct has been prepared and any undesirable sequences removed, e.g., procaryotic sequences, the construct may now be introduced into the target cell. Any convenient technique for introducing the DNA into the target cells may be employed. Techniques include spheroplast fusion, lipofection, electroporation, calcium phosphate-mediated DNA transfer or direct microinjection. After transformation or transfection of the target cells, target cells may be selected by means of positive and/or negative markers, as previously indicated, neomycin resistance and acyclovir or gancyclovir resistance. Those cells which show the desired phenotype may then be further analyzed by restriction analysis, electrophoresis, Southern analysis, PCR, or the like. By identifying fragments which show the presence of the lesion(s) at the target locus, one can identify cells in which homologous recombination has occurred to inactivate a copy of the target locus.

The above described process may be performed first with a heavy chain locus in an embryonic stem cell and then maturation of the cells to provide a mature fertile host. Then by breeding of the heterozygous hosts, a homozygous host may be obtained or embryonic stem cells may be isolated and transformed to inactivate the second IgH locus, and the process repeated until all the desired loci have been inactivated. Alternatively, the light chain locus may be the first. At any stage, the human loci may be introduced.

As already indicated, the target locus may be substituted with the analogous human locus. In this way, the human locus will be placed substantially in the same region as the analogous host locus, so that any regulation associated with the position of the locus will be substantially the same for the human immunoglobulin locus. For example, by isolating the entire $V_H$ gene locus (including V, D, and J sequences), or portion thereof, and flanking the human locus with sequences from the mouse locus, preferably sequences separated by at least about 5 kbp, in the host locus, preferably at least about 10 kbp in the host locus, one may insert the human fragment into this region in a recombinational event (s), substituting the human immunoglobulin locus for the variable region of the host immunoglobulin locus. In this manner, one may disrupt the ability of the host to produce an endogenous immunoglobulin subunit, while allowing for the promoter of the human immunoglobulin locus to be activated by the host enhancer and regulated by the regulatory system of the host.

Once the human loci have been introduced into the host genome, either by homologous recombination or random integration, and host animals have been produced with the endogenous immunoglobulin loci inactivated by appropriate breeding of the various transgenic or mutated animals, one can produce a host which lacks the native capability to produce endogenous immunoglobulin subunits, but has the capacity to produce human immunoglobulins with at least a significant portion of the human repertoire.

The functional inactivation of the two copies of each of the three host Ig loci, where the host contains the human IgH and the human Ig κ and/or λ loci would allow for the production of purely human antibody molecules without the production of host or host/human chimeric antibodies. Such a host strain, by immunization with specific antigens, would respond by the production of mouse B-cells producing specific human antibodies, which B-cells could be fused with mouse myeloma cells or be immortalized in any other manner for the continuous stable production of human monoclonal antibodies.

The subject methodology and strategies need not be limited to producing complete immunoglobulins, but provides the opportunity to provide for regions joined to a portion of the constant region, e.g., $C_{H1}$, $C_{H2}$, $C_{H3}$, or $C_{H4}$, or combination thereof. Alternatively, one or more of the exons of the $C_H$ and $C_\kappa$ or $C_\lambda$ regions may be replaced or joined to a sequence encoding a different protein, such as an enzyme, e.g., plasminogen activator, superoxide dismutase, etc.; toxin A chain, e.g., ricin, abrin, diphtheria toxin, etc.; growth factors; cytotoxic agent, e.g., TNF, or the like. See, for example, WO 89/07142; WO 89/09344; and WO 88/03559. By inserting the protein of interest into a constant region exon and providing for splicing of the variable region to the modified constant region exon, the resulting binding protein may have a different C-terminal region from the immunoglobulin. By providing for a stop sequence with the inserted gene, the protein product will have the inserted protein as the C-terminal region. If desired, the constant region may be entirely substituted by the other protein, by providing for a construct with the appropriate splice sites for joining the variable region to the other protein.

The antibodies or antibody analog producing B-cells from the transgenic host may be used for fusion to a mouse myeloid cell to produce hybridomas or immortalized by other conventional process, e.g., transfection with oncogenes. These immortalized cells may then be grown in continuous culture or introduced into the peritoneum of a compatible host for production of ascites.

The subject invention provides for the production of polyclonal human anti-serum or human monoclonal antibodies or antibody analogs. Where the mammalian host has been immunized with an immunogen, the resulting human antibodies may be isolated from other proteins by using an affinity column, having an Fc binding moiety, such as protein A, or the like.

For producing animals from embryonic stem cells, after transformation, the cells may be plated onto a feeder layer in an appropriate medium, e.g. fetal bovine serum enhanced DMEM. Cells containing the construct may be detected by employing a selective medium and after sufficient time for colonies to grow, colonies may be picked and analyzed for the occurrence of integration or homologous recombination. As described previously, the PCR may be used, with primers within or without the construct sequence, but at the target locus.

Those colonies which show homologous recombination may then be used for embryo manipulation and blastocyst injection. Blastocysts may be obtained from females by flushing the uterus 3–5 days after ovulation. The embryonic stem cells may then be trypsinized and the modified cells added to a droplet containing the blastocyst. At least one and up to thirty modified embryonic stem cells may be injected into the blastocoel of the blastocyst. After injection, at least one and no more then about fifteen of the blastocysts are returned to each uterine horn of pseudo-pregnant females. Females are then allowed to go to term and the resulting litter screened for mutant cells having the construct.

The mammals may be any non-human, particularly non-primate mammal, such as laboratory animals, particularly small laboratory animals, such as mice, rats, guinea pigs, etc., domestic animals, pets, etc.

The following examples are offered by way of illustration and not by way of limitation.

EXPERIMENTAL

Inactivation of the Mouse Heavy Chain J Genes Construction of the Inactivation Vector A 6.4 Kb EcoRI fragment, containing the mouse heavy chain J genes and flanking sequences, is cloned from a Balb/c mouse embryo genomic library using the probes described in Sakano et al., *Nature* 290:562–565, 1981. This fragment (mDJ) is inserted into EcoRI-digested pUC19 plasmid (pmDJ). A 2.9 Kb fragment, containing the 4 J genes, is deleted by XhoI-ScaI digestion (pmDδJNeo, see FIGS. 1A and 1B). An 1150 bp XhoI-BamHI fragment, containing a neomycin-resistance gene driven by the Herpes simplex virus thymidine kinase gene (HSV-tk) promoter and a polyoma enhancer is isolated from pMC1Neo (Thomas and Capecchi, *Cell,* 51, 503–512, 1987). A synthetic adaptor is added onto this fragment to convert the BamHI end into a ScaI end and the resulting fragment is joined to the XhoI-ScaI pmDδJ to form the inactivation vector (pmDδJ.Neo) in which the 5' to 3' orientation of the neomycin and the heavy chain promoters is identical. This plasmid is linearized by NdeI digestion before transfection to ES cells. The sequences driving the homologous recombination event are 3 kb and 0.5 kb fragments, located 5' and 3' to the neomycin gene, respectively.

The ES cell line E14TG2a (Hooper et al., *Nature,* 326:292–295, (1987) is cultured on mitomycin-treated primary embryonic fibroblast-feeder layers essentially as described (Doetschman et al., *J. Embryol. Exp. Morphol.* 87:27–45, 1985). The embryonic fibroblasts are prepared from embryos from C57BL/6 females that are mated 14 to 17 days earlier with a male homozygous for a neomycin transgene (Gossler et al., PNAS 83:9065–9069, 1986). These cells are capable of growth in media containing G418. Electroporation conditions are described by (Boggs et al., *Ex. Hematol.* (NY) 149:988–994, 1986). ES cells are trypsinized, resuspended in culture media at a concentration of $4\times10^7$/ml and electroporated in the presence of the targeting DNA at a concentration of 12 nM in the first experiment and 5 nM DNA in the second. A voltage of 300 V with a capacitance of 150–250 μF is found optimal with an electroporation cell of 5 mm length and 100 mm$^2$ cross-section. $5\times10^6$ electroporated cells are plated onto mitomycin-treated fibroblasts in 100 mm dishes in the presence of Dulbecco's modified Eagle's media (DMEM) supplemented with 15% fetal bovine serum (FBS) and 0.1 mM 2-mercaptoethanol. The media is replaced 24 hr after electroporation with media containing 200 μg/ml G418.

ES colonies resulting 10–14 days after electroporation are picked with drawn out capillary pipettes for analysis using PCR. Half of each picked colony is saved in 24-well plates already seeded with mitomycin-treated feeder cells. The other halves, combined in pools of 3–4, are transferred to Eppendorf tubes containing approximately 0.5 ml of PBS and analyzed for homologous recombination by PCR. Conditions for PCR reactions are essentially as described (Kim and Smithies, Nucleic Acids Res. 16:8887–8893, 1988). After pelleting, the ES cells are resuspended in 5 μl of PBS and are lysed by the addition of 55 μl of H$_2$O to each tube. DNAses are inactivated by heating each tube at 95° C. for 10 min. After treatment with proteinase K at 55° C. for 30 min, 30 μl of each lysate is transferred to a tube containing 20 μl of a reaction mixture including PCR buffer: 1.5 μg of each primer, 3U of Taq polymerase, 10% DMSO, and dNTPs, each at 0.2 mM. The PCR expansion employs 55 cycles using a thermocycler with 65 seconds melt at 92° C. and a 10 min annealing and extension time at 65° C. The two priming oligonucleotides are TGGCGGACCGCTATC-CCCCAGGAC and TAGCCTGGGTCCCTCCTTAC, which correspond respectively to a region 650 bases 3' of the start codon of the neomycin gene and sequences located in the mouse heavy chain gene, 1100 bases 3' of the insertion site. 20 μl of the reaction mix is electrophoresed on agarose gels and transferred to nylon membranes (Zeta Bind). Filters are probed with a $^{32}$P-labelled fragment of the 991 bp XbaI fragment of the J-C region.

Figure 2A:
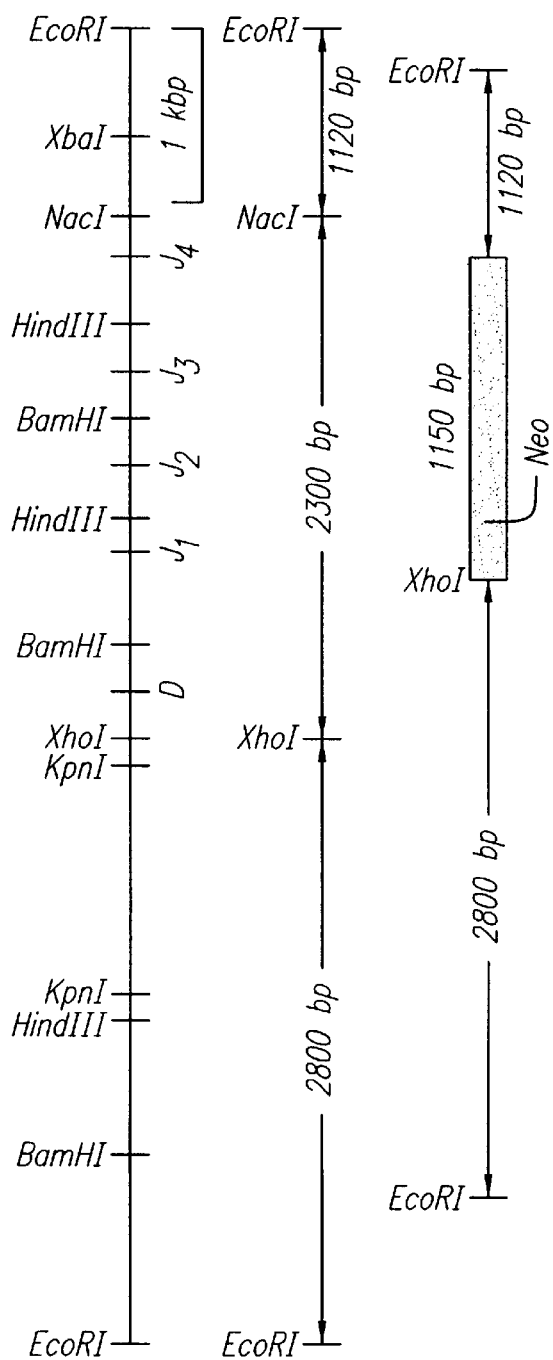
Figure 2B:
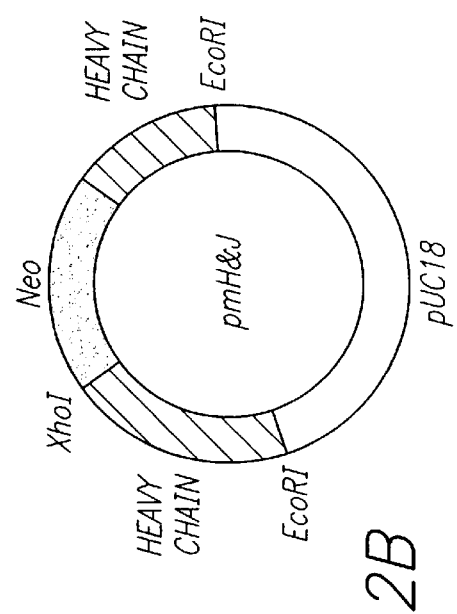

Inactivation of the Mouse Ig Heavy Chain J Genes in ES Cells Construction of the Inactivation Vector A 6.1-Kb EcoRI fragment, containing the mouse immunoglobulin heavy chain J region genes and flanking sequences, cloned from a Balb/c mouse embryo genomic library and inserted into pUC18 (pJH), was digested with XhoI and NaeI to delete an about 2.3 kbp fragment containing the four J genes (see FIG. 2A). An about 1.1 kbp XhoI-BamHI fragment, blunted at the BamHI site, containing a neomycin resistance gene driven by the Herpes simplex virus thymidine kinase gene (HSV-tk) promoter and polyoma enhancer was isolated from pMC1Neo (Thomas and Capecchi, *Cell,* 51, 503–512, 1987). This fragment was inserted into the XhoI-NaeI deleted pJH to form the inactivation vector (pmHδJ, see FIG. 2B), in which the transcriptional orientation of the neomycin and the heavy chain genes is the same. This plasmid was linearized by NdeI digestion before transfection to ES cells. The sequences driving the homologous recombination event are about 2.8 kbp and about 1.1 kbp fragments, located 5' and 3' to the neomycin gene, respectively.

Culturing, Electroporation, and Selection of ES Cells

The ES cell line E14TG2a (Koller and Smithies, 1989, *PNAS, USA,* 86, 8932–8935) was cultured on mitomycin C-treated embryonic fibroblast feeder layers as described (Koller and Smithies, 1989, supra USA, 86, 8932–8935). ES cells were trypsinized, resuspended in HBS buffer (pH 7.05; 137 mM NaCl, 5 mM KCl, 2 mM CaCl$_2$, 0.7 mM Na2HPO$_4$, 21 mM HEPES pH 7.1) at a concentration of $2\times10^7$/ml and electroporated in the presence of 50 μg/ml of the linearized inactivation vector. Electroporation was carried out with a BioRad Gene Pulser using 240 volts and 500 μF capacitance. $5\times10^6$ electroporated cells were plated onto mitomycin C-treated fibroblasts in 100 mm dishes in the presence of Dulbecco's modified Eagle's media (DMEM) supplemented with 15% fetal bovine serum and 0.1 mM 2-mercaptoethanol. The media was replaced 24 hr after electroporation with media containing 200 μg/ml G418. G418-resistant ES colonies resulting 12–14 days after electroporation were picked with drawn out capillary pipettes for analysis using the polymerase chain reaction (PCR). Half of each picked colony was transferred to an individual well of a 24-well plate, already seeded with mitomycin C-treated feeder cells. The other halves, combined in pools of four, were transferred to Eppendorf tubes containing 0.3 ml of PBS and cell lysates were prepared for PCR analysis as described by Joyner et al (*Nature,* 338:153–155, 1989). The PCR reaction included 5–20 μl of the cell lyste, 1 μM of each primer, 1.5u of Taq polymerase and 200 μM of dNTPs. The PCR amplification employed 45 cycles using a thermal cycler (Perkin-Elmer Cetus), with 1 min. melt at 94° C., 2 min. annealing at 55° C., and 3 min. extension at 72° C. The two priming oligonucleotides are ACGGTATCGCCGCTC-CCGAT and AGTCACTGTAAAGACTTCGGGTA, which correspond respectively to about 120 bases 5' of the BamHI site of the neomycin gene, and to the sequences located in the mouse heavy chain gene, about 160 bases 3' of the insertion site. Successful homologous recombination gives rise to an about 1.4 kbp fragment. 20 μl of the reaction mixture is electrophoresed on 1% agarose gels, stained with ethidium bromide and transferred to nylon membranes (Gene Screen). Filters were probed with a $^{32}$P-labelled EcoRI-PstI about 1.4 kbp fragment located in the mouse heavy chain, 3' of the insertion site (see FIG. 2). For further analysis, genomic DNA was prepared from ES cells, digested with restriction enzymes as recommended by the manufacturers, and fragments were separated on 1% agarose gels. DNA was transferred to nylon membranes (Gene Screen) and probed with the $^{32}$P-labelled fragment as described above.

Analysis of G418-Resistant ES Colonies

In the first experiment, PCR analysis of the pooled colonies detected one positive PCR signal of the expected size (about 1.4 kbp) out of 34 pools representing 136 G418-resistant colonies. The four individual colonies that had contributed to this positive pool were analyzed individually by PCR, and a positive clone, ES33D5, was identified. Similar analysis of 540 G418-resistant colonies obtained in the second experiment yielded 4 additional positive clones (ES41-1, ES61-1, ES65-1, ES110-1).

In order to verify the targeting disruption of one copy of the J genes, (the gene is autosomal and thus present in two copies), the PCR positive clones were expanded and genomic DNA was prepared, digested with HindIII or with SacI and analysed by Southern analysis as described using the EcoRI-PstI probe.

The replacement of the J genes by insertion of the neomycin gene by an homologous recombination event results in an HindIII fragment, detectable with the EcoRI-PstI probe, which is about 1.9 kbp longer than the equivalent fragment in the native locus, due to the loss of two HindIII sites located in the deleted J gene region (see FIGS. 2C and 2D). Southern analysis of each of the 5 positive clones by HindIII digestion gave a pattern which indicated that one of the two copies of the heavy chain J genes had been disrupted. Three labelled fragments were detected: one fragment (about 760 bp), identical in size to that present in untreated cells at the same intensity, one fragment (about 2.3 kbp) identical in size to that present in untreated cells, but of decreased intensity in the PCR positive clone, and an additional fragment about 4.2 kbp, the size predicted for an homologous recombination event, present only in the PCR-positive clones. Similarly, the replacement of the J genes by the neomycin gene by an homologous recombination event results in a loss of one SacI site and the appearance of a fragment, detectable with the EcoRI-PstI probe, which is about 570 bp smaller than the equivalent fragment in the native locus (see FIGS. 2C and 2D). Southern analysis of the clones by SacI digestion gave the expected pattern of one native and one targeted allele: about 4.0 kbp fragment, identical in size to that detected in untreated cells, but of decreased intensity in the 5 positive clones, and an additional fragment of about 3.4 kbp, the size predicted for a targeted homologous recombination event, present only in the identified clones. Rehybridization of the Southern blots with a probe for the neomycin gene shows that only the 4.2 kbp and 3.4 kbp fragments, resulting from the HindIII and the SacI digestion, respectively, hybridized to the probe as predicted by the targeting event.

Production of Human Ig in Transgenic Mice Example: Production of Human Heavy Chain in Transgenic Mice DNA Vector An SpeI fragment, spanning the human heavy chain VH6-D-J-C$\mu$-C$\delta$ region (Berman et al., *EMBO J.* (1988) 7: 727–738; see FIG. 3A) is isolated from a human library cloned into a yeast artificial chromosome (YAC) vector (Burke, et al., *Science*, 236: 806–812) using DNA probes described by Berman et al. (*EMBO J.* (1988) 7:727–738). One clone is obtained which is estimated to be about 100 Kb. The isolated YAC clone is characterized by pulsed-field gel electrophoresis (Burke et al., supra; Brownstein et al., *Science*, 244: 1348–13451), using radiolabelled probes for the human heavy chain (Berman et al., supra).

Introduction of YAC Clones into Embryos

High molecular weight DNA is prepared in agarose plugs from yeast cells containing the YAC of interest (i.e., a YAC containing the aforementioned SpeI fragment from the IgH locus). The DNA is size-fractionated on a CHEF gel apparatus and the YAC band is cut out of the low melting point agarose gel. The gel fragment is equilibrated with polyamines and then melted and treated with agarase to digest the agarose. The polyamine-coated DNA is then injected into the male pronucleus of fertilized mouse embryos which are surgically introduced into the uterus of a psueudopregnant female as described above. The transgenic nature of the newborns is analyzed by a slot-blot of DNA isolated from tails and the production of human heavy chain is analyzed by obtaining a small amount of serum and testing it for the presence of Ig chains with rabbit anti-human antibodies.

As an alternative to microinjection, YAC DNA is transferred into murine ES cells by ES cell: yeast protoplast fusion (Traver et al., 1989 *Proc. Natl. Acad. Sci.*, USA, 86:5898–5902; Pachnis et al., 1990, ibid 87: 5109–5113). First, the neomycin-resistance gene from pMClNeo and a yeast selectable marker are inserted into nonessential YAC vector sequences in a plasmid. This construct is used to transform a yeast strain containing the IgH YAC, and pMClNeo is integrated into vector sequences of the IgH YAC by homologous recombination. The modified YAC is then transferred into an ES cell by protoplast fusion (Traver et al., 1989; Pachnis et al., 1990), and resulting G418-resistant ES cells which contain the intact human IgH sequences are used to generate chimeric mice.

Production of Human Ig By Chimeric Mice Construction of Human Heavy Chain Replacement Vector The replacing human sequences include the SpeI 100 kbp fragment of genomic DNA which encompasses the human VH6-D-J-C$\mu$-C$\delta$ heavy chain region isolated from a human-YAC library as described before. The flanking mouse heavy chain sequences, which drive the homologous recombination replacement event, contain a 10 kbp BamHI fragment of the mouse C$\epsilon$-C$\alpha$ heavy chain and a 5' J558 fragment comprising the 5' half of the J558 fragment of the mouse heavy chain variable region, at the 3' and 5' ends of the human sequences, respectively (FIG. 3B). These mouse sequences are isolated from a mouse embryo genomic library using the probes described in Tucker et al., *PNAS USA*, 78: 7684–7688, 1981, and Blankenstein and Krawinkel (1987, supra), respectively. The 1150 bp XhoI to BamHI fragment, containing a neomycin-resistance gene driven by the Herpes simplex virus thymidine kinase gene (HSV-tk) promoter and a polyoma enhancer is isolated from pMClNeo (Koller and Smithies, 1989, supra). A synthetic adaptor is added onto this fragment to convert the XhoI end into a BamHI end and the resulting fragment is joined to the BamHI mouse C$\epsilon$-C$\alpha$ in a plasmid.

Figure 3A:
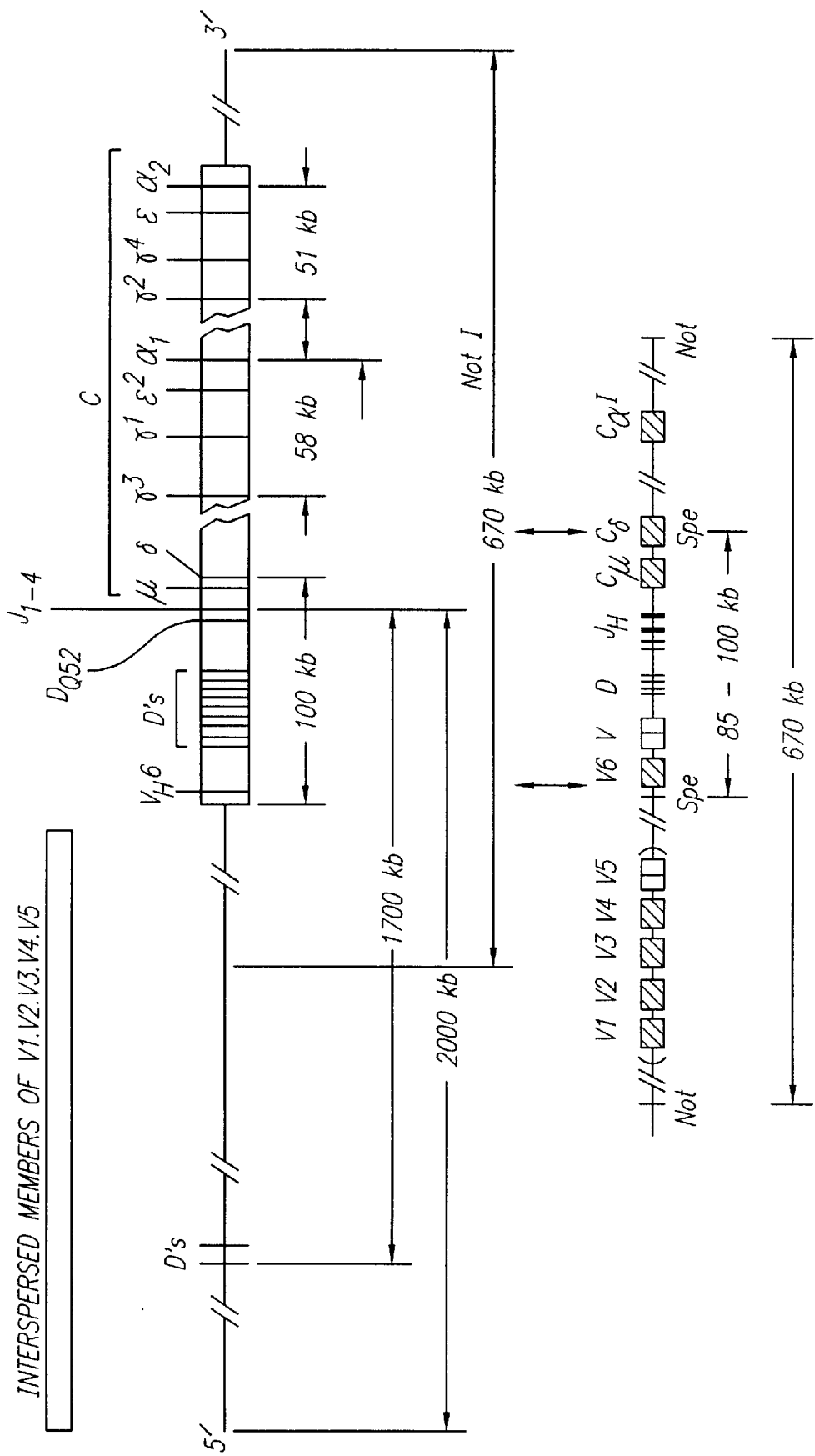
FIGS. 3A–C.
Figure 3B:
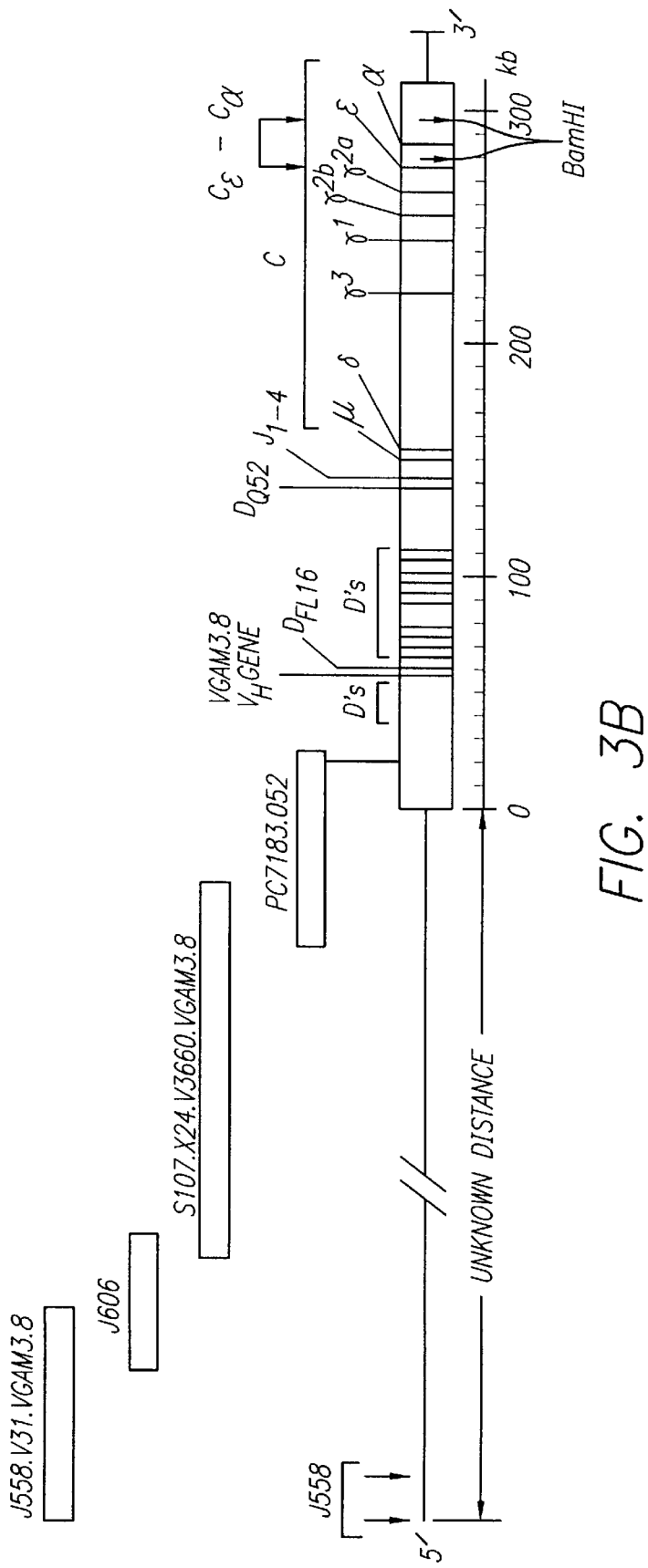
Figure 3C:
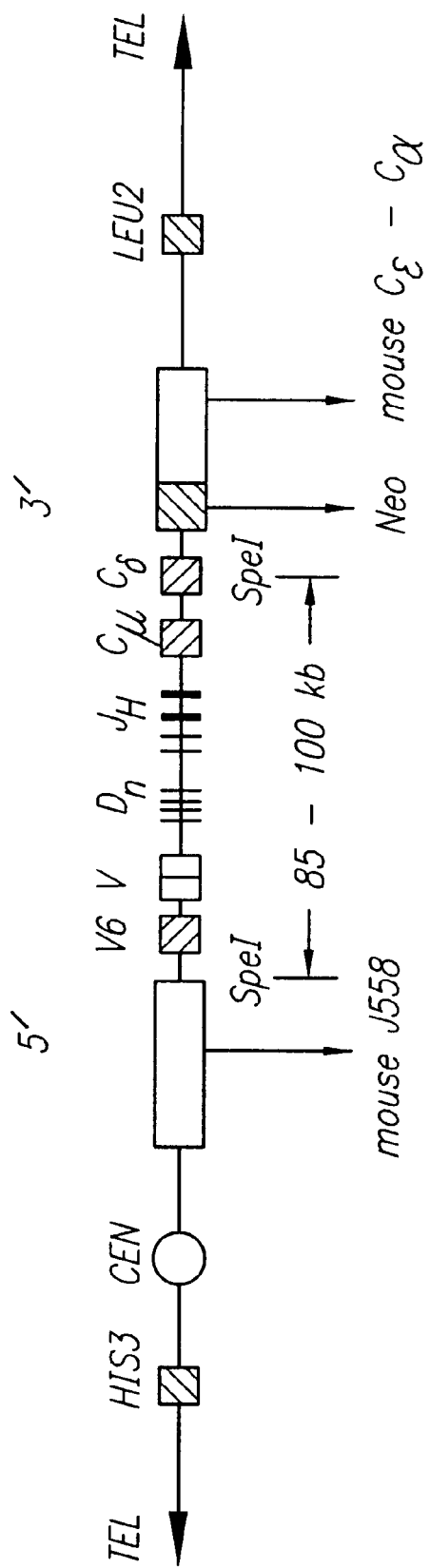

From the YAC clone containing the human heavy chain locus, DNA sequences from each end of the insert are recovered either by inverse PCR (Silverman et al., *PNAS*, 86:7485–7489, 1989), or by plasmid rescue in *E. coli*, (Burke et al., 1987; Garza et al. *Science*, 246:641–646, 1989;

Traver et al., 1989) (see FIG. 3A). The isolated human sequence from the 5'V6 end of the YAC is ligated to the mouse J558 sequence in a plasmid and likewise, the human sequence derived from the 3Cδ end of the YAC is ligated to the Neo gene in the plasmid containing Neo and mouse Cε-Cα described above. The human V6-mouse J558 segment is now subcloned into a half-YAC cloning vector that includes a yeast selectable marker (HIS3) not present in the original IgH YAC, a centromere (CEN) and a single telomere (TEL). The human Cδ-Neo-mouse Cε-Cα is likewise subcloned into a separate half-YAC vector with a different yeast selectable marker (LEU2) and a single TEL. The half-YAC vector containing the human V6 DNA is linearized and used to transform a yeast strain that is deleted for the chromosomal HIS3 and LEU2 loci and which carries the IgH YAC. Selection for histidine-prototrophy gives rise to yeast colonies that have undergone homologous recombination between the human V6 DNA sequences and contain a recombinant YAC. The half-YAC vector containing the human Cδ DNA is then linearized and used to transform the yeast strain generated in the previous step. Selection for leucine-prototrophy results in a yeast strain containing the complete IgH replacement YAC (see FIG. 3C). This YAC is isolated and introduced into ES cells by microinjection as described previously for embryos.

In accordance with the above procedures, an antigenic or chimeric non-primate host, particularly a mouse host, may be produced which can be immunized to produce human antibodies or analogs specific for an immunogen. In this manner, the problems associated with obtaining human monoclonal antibodies are avoided, since mice can be immunized with immunogens which could not be used with a human host. Furthermore, one can provide for booster injections and adjuvants which would not be permitted with a human host. The resulting B-cells may then be used for immortalization for the continuous production of the desired antibody. The immortalized cells may be used for isolation of the genes encoding the immunoglobulin or analog and be subjected to mutation by in-vitro mutagenesis or other mutagenizing technique to modify the properties of the antibodies. These mutagenized genes may then be returned to the immortalized cells for homologous recombination to provide for a continuous mammalian cellular source of the desired antibodies. The subject invention provides for a convenient source of human antibodies, where the human antibodies are produced in analogous manner to the production of antibodies in a human host. The mouse cells conveniently provide for the activation and rearrangement of human DNA in mouse cells for production of human antibodies.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing a transgenic mouse lacking expression of an endogenous immunoglobulin heavy chain, comprising:
   (a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker; and
   (b) producing from the embryonic stem cell a transgenic mouse whose somatic and germ cells contain the gene encoding the selectable marker,
wherein the transgenic mouse lacks expression of an endogenous immunoglobulin heavy chain.

2. A method for producing a transgenic mouse lacking expression of an endogenous immunoglobulin heavy chain, comprising:
   (a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker; and
   (b) producing from the embryonic stem cell a transgenic mouse whose somatic and germ cells contain an immunoglobulin heavy chain locus in which all of the J segment genes are deleted,
wherein the transgenic mouse lacks expression of an endogenous immunoglobulin heavy chain.

3. A method for producing a transgenic mouse and its progeny lacking expression of endogenous immunoglobulin heavy chains, comprising;
   (a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker;
   (b) producing from the embryonic stem cell a transgenic mouse whose somatic and germ cells contain an immunolobulin heavy chain locus in which all of the J segment genes are deleted, and
   (c) breeding the transgenic mouse as needed to produce a transgenic mouse and its progeny lacking expression of endogenous immunoglobulin heavy chains.

4. A method for producing a transgenic mouse and its progeny lacking expression of endogenous immunoglobulin heavy chains, comprising:
   (a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker;
   (b) producing from the embryonic stem cell a transgenic mouse whose somatic and germ cells contain the gene encoding the selectable marker, and
   (c) breeding the transgenic mouse as needed to produce a transgenic mouse and its progeny lacking expression of endogenous immunoglobulin heavy chains.

5. The method according to any one of claims 1–4, wherein the gene encoding a selectable marker is a neomycin resistance gene.

6. A method for preventing the expression of an endogenous immunoglobulin heavy chain in a transgenic mouse, comprising:
   (a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker; and (b) producing from the embryonic stem cell a transgenic mouse whose somatic and germ cells contain the gene encoding the selectable marker, wherein the transgenic mouse lacks expression of an endogenous immunoglobulin heavy chain.

7. A method for preventing the expression of an endogenous immunoglobulin heavy chain in a transgenic mouse, comprising:

(a) deleting the J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker; and (b) producing from the embryonic stem cell a transgenic mouse whose somatic and germ cells contain an endogenous immunoglobulin heavy chain locus in which all of the J segment genes are deleted, wherein the transgenic mouse lacks expression of an endogenous immunoglobulin heavy chain.

8. A method for preventing the expression of endogenous immunoglobulin heavy chains in a transgenic mouse and its progeny, comprising:

(a) deleting J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker;

(b) producing from the embryonic stem cell a transgenic mouse whose somatic and germ cells contain an immunoglobulin heavy chain locus in which all of the J segment genes are deleted, and (c) breeding the transgenic mouse as needed to produce a transgenic mouse and its progeny lacking expression of endogenous immunoglobulin heavy chains.

9. A method for preventing the expression of endogenous immunoglobulin heavy chains in a transgenic mouse and its progeny, comprising:

(a) deleting J segment genes from at least one endogenous heavy chain locus in a mouse embryonic stem cell to prevent rearrangement of the locus and to prevent formation of a transcript of a rearranged immunoglobulin heavy chain locus, the deletion being effected by a targeting vector comprising a gene encoding a selectable marker;

(b) producing from the embryonic stem cell a transgenic mouse whose somatic and germ cells contain the gene encoding the selectable marker, and (c) breeding the transgenic mouse as needed to produce a transgenic mouse and its progeny lacking expression of endogenous immunoglobulin heavy chains.

10. The method according to any one of claims 6–9, wherein the gene encoding a selectable marker is a neomycin resistance gene.

11. A method for producing a mouse embryonic stem cell with at least one inactivated endogenous immunoglobulin heavy chain locus, comprising deleting the J segment genes of at least one endogenous immunoglobulin heavy chain locus in the mouse embryonic stem cell to prevent rearrangement of the locus and to prevent the formation of a transcript of a rearranged immunoglobulin heavy chain, the deletion being effected by a targeting vector comprising a gene encoding a selectable marker.

12. The method according to claim 11, wherein the gene encoding a selectable marker is a neomycin resistance gene.

13. The method according to any one of claims 1, 2, 6 or 7, further comprising producing progeny of the transgenic mouse by breeding.

\* \* \* \* \*